United States Patent
Lee et al.

(10) Patent No.: US 11,389,605 B2
(45) Date of Patent: Jul. 19, 2022

(54) LOW FLOW PERCUSSIVE RESPIRATORY APPARATUS AND RELATED TREATMENT

(71) Applicant: VORTRAN MEDICAL TECHNOLOGY 1, INC., Sacramento, CA (US)

(72) Inventors: James I-Che Lee, Sacramento, CA (US); Abdolreza Saied, Carmichael, CA (US); Glen M. Thomson, Sequim, WA (US)

(73) Assignee: Vortran Medical Technology I, Inc., Sacramento, CA (US)

( * ) Notice: Subject to any disclaimer, the term of this patent is extended or adjusted under 35 U.S.C. 154(b) by 703 days.

(21) Appl. No.: 16/273,381

(22) Filed: Feb. 12, 2019

(65) Prior Publication Data

US 2019/0247599 A1 Aug. 15, 2019

Related U.S. Application Data

(60) Provisional application No. 62/629,415, filed on Feb. 12, 2018.

(51) Int. Cl.
*A61M 16/00* (2006.01)
*A61M 16/20* (2006.01)
(Continued)

(52) U.S. Cl.
CPC ........ *A61M 16/0006* (2014.02); *A61M 11/06* (2013.01); *A61M 16/049* (2014.02);
(Continued)

(58) Field of Classification Search
CPC ............ A61M 16/0006; A61M 16/049; A61M 16/127; A61M 16/201; A61M 11/06;
(Continued)

(56) References Cited

U.S. PATENT DOCUMENTS

| | | | |
|---|---|---|---|
| 4,747,402 A | 5/1988 | Reese et al. | |
| 6,067,984 A | 5/2000 | Piper | |

(Continued)

FOREIGN PATENT DOCUMENTS

| | | |
|---|---|---|
| EP | 2186538 | 5/2010 |
| JP | H11-267216 | 10/1999 |

(Continued)

OTHER PUBLICATIONS

Extended European Search Report for European Patent Application No. 19156751.0, dated Jun. 21, 2019, 7 pages.

(Continued)

*Primary Examiner* — Steven O Douglas
(74) *Attorney, Agent, or Firm* — Sheridan Ross P.C.

(57) ABSTRACT

A valve assembly attached to a capacitor such that pressurizing the capacitor to a first positive pressure threshold induces the valve assembly to open, the pressurized air is released to the patient, and then as the pressure in the capacitor drops to a second pressure threshold the valve closes and the capacitor begins to build pressure until the first positive pressure threshold is achieved and the process repeats. Relative to the valve assembly and integrated therein, is an incrementally adjustable index knob to vary the rate of a biasing force performing work against the actionable valve face of the diaphragm functional surface to set the performance of the valve assembly, thereby increasing the potential for correct operation across a range of oscillating rates supporting a broad spectrum of patient therapies and types.

20 Claims, 13 Drawing Sheets

(51) Int. Cl.
*A61M 16/04* (2006.01)
*A61M 11/06* (2006.01)
*A61M 16/14* (2006.01)
*A61M 16/12* (2006.01)
*A61M 11/00* (2006.01)
*A61H 23/00* (2006.01)
*A61M 15/00* (2006.01)
*A61M 16/08* (2006.01)

(52) U.S. Cl.
CPC .......... *A61M 16/127* (2014.02); *A61M 16/14* (2013.01); *A61M 16/20* (2013.01); *A61M 16/201* (2014.02); *A61H 23/006* (2013.01); *A61H 2205/084* (2013.01); *A61M 11/005* (2013.01); *A61M 15/0021* (2014.02); *A61M 16/042* (2014.02); *A61M 16/0808* (2013.01); *A61M 16/0816* (2013.01); *A61M 2016/0027* (2013.01); *A61M 2202/0208* (2013.01); *A61M 2209/084* (2013.01)

(58) Field of Classification Search
CPC .. A61M 16/14; A61M 16/20; A61M 15/0021; A61M 16/042; A61M 11/005; A61M 16/0808; A61M 16/0816; A61M 2016/0027; A61M 2202/0208; A61M 2209/084; A61H 23/006; A61H 2205/084
See application file for complete search history.

(56) References Cited

U.S. PATENT DOCUMENTS

| | | | |
|---|---|---|---|
| 6,425,396 B1 * | 7/2002 | Adriance | A61M 16/00 128/204.26 |
| 6,766,800 B2 | 7/2004 | Chu et al. | |
| 8,225,785 B2 | 7/2012 | Richards et al. | |
| 8,783,251 B2 | 7/2014 | Koledin | |
| 2020/0139076 A1 * | 5/2020 | Baillie | A61M 16/022 |

FOREIGN PATENT DOCUMENTS

| | | |
|---|---|---|
| WO | WO 02/043643 | 6/2002 |
| WO | WO 2013/054244 | 4/2013 |

OTHER PUBLICATIONS

Communication pursuant to Rule 69 for European Patent Application No. 19156751.0, dated Aug. 20, 2019, 2 pages.

* cited by examiner

LOW FLOW PERCUSSIVE RESPIRATORY APPARATUS AND RELATED TREATMENT

CROSS REFERENCE TO RELATED APPLICATIONS

The present application claims priority to U.S. Provisional Application 62/629,415, entitled "Low Flow Percussive Respiratory Apparatus and Related Treatment", filed on 12 Feb. 2018, the entirety of which is incorporated herein by this reference.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

Many chronic conditions such as bronchiectasis, cystic fibrosis (CF), neuromuscular disease and chronic obstructive pulmonary disease (COPD) are associated with an increase in both the quantity and viscosity of respiratory secretions. Airway inflammation, bronchospasm and the increase in sputum volume are constant in these patients and are responsible for an increase in airway resistance and air trapping. This air trapping and increased airway resistance result in hyperinflation and intrinsic positive expiratory pressure (PEEPi), which are common features during acute exacerbations of COPD patients and are responsible for increasing the work required to breathe and respiratory muscle failure. Other conditions are associated with a decreased ability to clear secretions, such as those with impaired ciliary function or cough, with the latter being very common during mechanical ventilation, after strokes or surgical procedures, and in neuromuscular disorders. Studies have shown that when these secretions are not adequately cleared, complications arise such as atelectasis, mucus plugging, and recurrent pneumonia. Inadequate mucus clearance in patients in the intensive care unit (ICU) can lead to poor clinic outcomes such as prolonged time on mechanical ventilation, increase in need for tracheostomies, decreased quality of life, overall worsening lung function and an increase in mortality.

The intrapulmonary percussive valve ("IPV") is designed to both treat active pulmonary disease and to prevent the development of disease caused by secretion retention. The IPV device was developed by Forrest M. Bird in 1979. IPV is a ventilatory technique that delivers small bursts of high flow respiratory gas into the lung at high rates. This causes airway pressures to oscillate between a range of frequencies or cycles per minute and the airway walls vibrate in synchrony with these oscillations. During inspiration the high frequency gas pulse expands the lungs and vibrates and enlarges the airways. This technique may be associated with nebulization and has the potential to improve secretion clearance. During the percussive bursts of air into the lungs, a continued pressure is maintained, while a high velocity percussive inflow opens airways and enhances intra-bronchial secretion mobilization. Specific goals of therapy include promoting the mobilization of bronchial secretions, improving the efficiency and distribution of ventilation, providing an alternative delivery system for bronchodilator therapy, providing intrathoracic percussion and vibration, and providing an alternative system for the delivery of positive pressure to the lungs.

Examples of an IPV are described in U.S. Pat. No. 6,067,984 to Piper and U.S. Pat. No. 6,766,800 to Chu et al., both of which are incorporated herein by reference in their entireties. The percussive respiratory device is comprised of a functional surface area defined by a dual area piston having a face that rests against an interior end of a primary port associated with a fluidic manifold, thus sealing the manifold during charging with a fluid such as pressurized gas. The dual area piston comprises a primary surface area defined as the area exposed to the primary port during charging thereby defining a closed position for the valve function, and a much larger area which comprises the total area of the piston face which is in fluid communication when the piston is moved away from the primary port thereby defining an open position. When the dual area piston is closed, it prevents compressed gas from escaping and thus causing a discharge before sufficient trigger pressure is established. During charging, the pressure in the manifold or capacitive chamber increases until the force of the pressure on the primary area of the dual area piston overcomes a biasing force against the piston. Once the dual area piston begins to open, the complete surface area of the piston is exposed to the pressure of inrushing fluid causing the piston to move away from the interior end of the primary port to an open position. The manifold pressure that causes the piston to move into the fully open position is the set PIP and when in a closed position as a residual PEEP (Positive End-Expiratory Pressure), which is taught as being set through a range of adjustability by controlling the degree of biasing force against the piston. Once the piston opens, it will remain open until the manifold pressure on the surface area of the piston drops to a value less than the force of the biasing force. During discharge, the fluid in the manifold pass by the piston and out of the system through an adjustable flow restrictor used to control the rate at which discharged gases are vented into the atmosphere, resulting in the control of a patient discharge duration. Once the pressure drops to a value low enough to allow the biasing force to push the piston closed, the discharge ends, the manifold pressure begins to rise against the primary surface of the piston and the cycle is repeated.

While control of the biasing force can be a ready means for altering the pressure necessary to trigger a threshold valve, the ability to readily alter a threshold valve's ability to respond to both a trigger pressure and an open state maintenance pressure by an easy manipulation of the device itself has previously not been achieved. To allow the trigger pressure and maintenance pressure to be controlled through the ratio of the trigger pressure to the maintenance pressure is a particular advantage when the threshold valve is to control a residual manifold pressure relative to the trigger pressure. There remains an unmet need for an improved method and means for managing the cyclic rate of the valve assembly, and in particular to manage the cyclic rate so as to impart an oscillating or percussive quality to a continuous or semi continuous flow of fluid, such as a therapeutic inhaled gas, such that operation is repeatable at a known therapeutic performance level, is attainable in terms of both operation of one assembly over a protracted period and for attaining equivalent defined performance between any two valve assemblies.

The percussive respiratory device illustrated in FIG. 7 of the '984 patent was sold by Vortran Medical Technology, Inc., the assignee of the present application, under the brand name PNEB. As described in the '984 patent, the device 130 comprises a nebulizer assembly 100, a pneumatic capacitor assembly 132 and a pressure modulator apparatus 10. This device 130 is illustrated herein in FIG. 1A in an assembled elevation view. FIG. 1B herein shows the fluid flow path within this device 130. This system consumes a high volume of a continuous flow of pressurized input gas to effect operation. With reference to FIG. 1B, as well as FIGS. 6A, 6B and 7 of the '984 patent, an input fluid, such as pressurized oxygen, is received at gas inlet 136. Here the fluid is diverted into two paths. The first path A (solid line) goes through channel 142 into the capacitive chamber 154. The second path B (large dashes) splits from path A at the choke tube 144 and travels through the nebulizer assembly 100 and to the patient via mouthpiece 104. Pressurized input gas accumulates in the chamber 154 until the pressure overcomes the resistance provided by spring 150 and the percussive valve assembly 132 opens. The input gas then exits through output 156 and path A continues into the chamber 42 of the pressure modulator apparatus 10, exits chamber 42 through port 134 and travels to the patient mouthpiece 104 via connectors 120 and 122. Paths A and B merge at the patient mouthpiece. Upon patient exhalation, the exhaled gas travels along path C (small dashes). Path C goes from the mouthpiece 104, through the connectors 120 and 122 and exits the device 10 via the exhalation restrictor 20. However, paths A and C travel through and share chamber 42. Because exhalation path C is always open, a portion of the input gas traveling along path A necessarily exits the device 10 and is not received by the patient. Thus, for this device to properly meet patient needs the input gas must be introduced into the device 10 at an elevated pressure or flow rate to accommodate the loss of input gas through the exhalation restrictor 20. Accordingly, there remains an unmet need for reducing the consumption rate of pressurized input fluid by the device while maintaining proper oscillating operation and performance over a broader range of functional conditions within the device, for example, a system that is more efficient or less wasteful than existing systems. A further problem with this device is that the exhaled fluid must pass through the same port as the incoming gas. The resistance created by the incoming gas inhibits movement of the exhalation leading to a patient potentially rebreathing or inhaling some portion of exhaled gas and, perhaps, exhaled fluids. Thus, there also remains a need for an improved percussive respiratory device that reduces resistance to patient exhalation.

SUMMARY OF THE DISCLOSURE

This disclosure is directed to means and methods for providing respiratory treatment to a patient. In particular, a unique valve is used by which a pressure and flow oscillation is imparted to an inspired and expired air volume. This oscillation offers a benefit to the patient in that occluded lung passageways, bronchial tubes and alveoli may be reopened and breathing function restored or otherwise improved.

According to aspects of the present disclosure, in one embodiment a valve assembly is attached to a capacitor such that upon pressurizing to a first positive pressure threshold induces the valve assembly to open, the pressurized air is released to the patient, and then as the pressure in the capacitor drops to a second pressure threshold the valve closes and the capacitor begins to build pressure until the first positive pressure threshold is achieved and the process repeats. In one embodiment, the valve assembly includes a diaphragm functional surface affixed to a moveable valve face and a fluidic communication port, wherein the fluidic communication port is in close proximity (and optimally in direct contact) with the functional surface of the moveable valve face, the contact region there between the valve assembly and fluidic communication port describing an actionable surface area. Relative to the valve assembly and integrated therein, is an incremental index knob. By introduction of an incremental index knob the rate of a biasing force performing work against the actionable valve face of the diaphragm functional surface allows for defined, reproducible, and predictable performance of the valve assembly, thereby increasing the potential for correct operation across a range of oscillating rates supporting a broad spectrum of patient therapies and types.

Also, according to aspects of the present disclosure, the diaphragm functional surface is part of a percussive respiratory device. Compressed gas is delivered directly to a pneumatic capacitor of static (fixed or inelastic construction) or dynamic (variable or elastic construction) response, thus charging the pneumatic capacitor with a fluidic pressure. During discharge, input gas at least partially flows through the percussive respiratory device to a patient-oriented outlet. The apparatus cycles the pressure within the pneumatic capacitor by controlling at what pressure the diaphragm functional surface is triggered to open and the degree by which the biasing force on the diaphragm functional surface is forced to close. Through adjustment of the input pressure and adjustment of an adjustable index knob, the corresponding frequency and amplitude of the oscillatory action is finitely and reproducibly controlled.

In a further embodiment according to aspects of the present disclosure, the diaphragm functional surface is part of a valve assembly in a percussive respiratory device. Compressed gas is delivered directly to a pneumatic capacitor, thus charging the pneumatic capacitor. During discharge, all gas flows through the percussive respiratory device to a patient-oriented outlet. The diaphragm functional surface cycles the pneumatic capacitor by controlling at what pressure charging ends and discharge begins. The duration of charging is controlled by the flow rate of incoming fluid and is affected by the compliance of the pneumatic capacitor. The duration of discharge is controlled by action of the adjustable index knob upon the biasing means against the diaphragm functional surface. Increasing and decreasing the position of the index knob correspondingly increases and decreases the rate by which the discharged gas of the pneumatic capacitor is exhausted into the patient. With the pneumatic capacitor pressure dropping to a specified level less than the counteracting biasing means, the diaphragm functional surface of the percussive respiratory device closes, and the pneumatic capacitor begins is recharged by the flow of gas. Thus, the cycle is repeated indefinitely so long as there is at least intermittent pressurized fluid source to the percussive respiratory device. The diaphragm functional surface is associated with a primary cavity of a pneumatic capacitance which may be caused by the user to cycle at a variety of frequencies and amplitudes, thus providing a different type of ventilatory effect and therapeutic performance on the patient which is in constant fluid communication with the primary cavity of the percussive respiratory device.

In a further embodiment, the percussive respiratory device comprises an entrainment valve assembly. The entrainment valve assembly includes an entrainment inlet port where by a pressurized fluid source, such as compressed oxygen, is connected. Pressurized fluid is conducted through the inlet port and into an entrainment jet. The entrainment jet imparts a laminar flow to the pressurized fluid whereby it is then conducted into an entrainment outlet port. As the laminar flow is conducted from the inlet port to the outlet port, a negative pressure is created proximal to the entrainment jet. Incremental additional fluid is drawn in by the negative pressure through one or more secondary inlet ports. The degree of flow through the one or more secondary inlet ports is defined by an entrainment mixing adjustment which engages upon an indexing element to allow for finite adjustment. The volume of fluid conducted through the entrainment as inlet port plus the volume of fluid drawn in by the secondary inlet port are intermixed and ejected as an essentially homogenous fluid via the entrainment jet outlet port.

In a further embodiment, a percussive respiratory device including a diaphragm functional surface exhibits a complete cycling rate from open to closed fluid conditions of between about 1 and about 100 cycles per second and, more preferably, about 10 and about 20 cycles per second.

In a further embodiment, a percussive respiratory device including a diaphragm functional surface exhibiting a cycling rate when provided pressurized air, oxygen or mixtures thereof at a pressure of between about 8 and about 20 cm-water and, more preferably, at about 10 and about 18 cm-water.

In a further embodiment, a percussive respiratory device including a diaphragm functional surface exhibits a cycling rate when provided pressurized air, oxygen or mixtures thereof at a flow of between 8 and 30 liters per minute and, more preferably, between about 10 and about 25 liters per minute.

In a further embodiment, a percussive respiratory device including an entrainment valve assembly exhibits ratio of inlet pressurized fluid to volume of incremental additional fluid drawn in by the secondary inlet port of between about 10:90 to about 90:10 and, more preferably, between about 30:70 to about 70:30.

According to aspects of the present disclosure a percussive respiratory device is disclosed, including an incremental index knob, wherein the percussive respiratory device may be used to provide therapeutic benefit to a patient physically located within an environment sensitive to electrical, magnetic, electromagnetic, and radiopaque interference.

According to aspects of the present disclosure a percussive respiratory device is disclosed, including an entrainment valve assembly adapted for use by a singular or given patient and then disposed thereafter.

According to aspects of the present disclosure a percussive respiratory device is disclosed, including an adjustable index knob and an entrainment valve assembly adapted for use for a singular or given patient and then disposed thereafter.

According to aspects of the present disclosure a percussive respiratory device is disclosed, including an adjustable index knob with a self-retaining locking mechanism.

Another aspect of the technology is to provide a percussive respiratory device, including an adjustable index knob with self-retaining locking mechanism, wherein said self-retaining locking mechanism allows for limitation of the number or degree of rotation available to a user of said percussive respiratory device.

According to aspects of the present disclosure a percussive respiratory device is disclosed, including an adjustable index knob with a self-retaining locking mechanism wherein said self-retaining locking mechanism prevents over-rotation or disassembly of incremental index knob relative to said percussive respiratory device.

In any embodiment above, an adjustable index knob may be associated with a percussive respiratory device and operate under a complete and repeating cycle mode. Additionally, the assembly may be used in conjunction with a nebulizer, providing therapeutic relief, in addition to the delivered ventilatory support.

According to aspects of the present disclosure, a percussive respiratory device may be used in conjunction with a nebulizer to deliver intermittent positive pressure aerosolized medication to the patient at varying oscillation rates. Further, the nebulizer can be used in various spatial orientations relative to the percussive respiratory device axis of diaphragm surface operation and in various spatial orientations relative to the percussive respiratory device pneumatic capacitor.

According to aspects of the present disclosure, a percussive respiratory device is provided which utilizes a mouth piece having a divided lumen, wherein said divided lumen allows for inhalation and exhalation volumes to remain independent and free of intermixing, wherein the divided lumen allows for exhalation ventilation, and/or wherein said divided lumen allows for countercurrent exhalation ventilation. A further aspect of the present disclosure is to provide a divided lumen mouth piece having associated therewith one or more exterior ventilation ports in direct communication with the exhalation aspect of the divided lumen. A further aspect of the present disclosure is to provide a divided lumen mouth piece having associated therewith an inhalation pathway and an exhalation pathway wherein the inhalation and exhalation pathways are in either symmetrical or asymmetrical orientation as viewed in cross-section of the divided lumen. Another aspect according to the present disclosure is providing a divided lumen allowing separate inhalation and exhalation pathways without increasing the outer diameter of the patient mouthpiece. A further aspect of the present disclosure is to provide a divided lumen mouth piece having associated therewith a nebulizer which allows for direct flow of medicament upon inhalation through a first lumen and exhaust of exhaled gas through a contracurrent secondary lumen.

Further embodiments and aspects of the technology described herein will be brought out in the following portions of the specification, wherein the detailed description is for the purpose of fully disclosing preferred embodiments of the technology without placing limitations thereon. These and other advantages will be apparent from the disclosure of the invention(s) contained herein. The above-described embodiments, objectives, and configurations are neither complete nor exhaustive. As will be appreciated, other embodiments of the invention are possible using, alone or in combination, one or more of the features set forth above or described in detail below. Further, the summary of the invention is neither intended nor should it be construed as being representative of the full extent and scope of the present invention. The present invention is set forth in various levels of detail in the summary of the invention, as well as, in the attached drawings and the detailed description of the invention and no limitation as to the scope of the present invention is intended to either the inclusion or non-inclusion of elements, components, etc. in this summary of the invention. Additional aspects of the present invention will become more readily apparent from the detailed description, particularly when taken together with the drawings. Moreover, reference made herein to "the present invention" or aspects thereof should be understood to mean certain embodiments of the present invention and should not necessarily be construed as limiting all embodiments to a particular description.

DESCRIPTION OF THE DRAWING

The accompanying drawings, which are incorporated in and constitute a part of the specification, illustrate embodiments of the invention and together with the general description of the invention given above and the detailed description of the drawings given below, serve to explain the principles of these inventions.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which are not necessary for an understanding of the present invention, such as conventional details of fabrication and assembly.

DETAILED DESCRIPTION

Figure 1A:
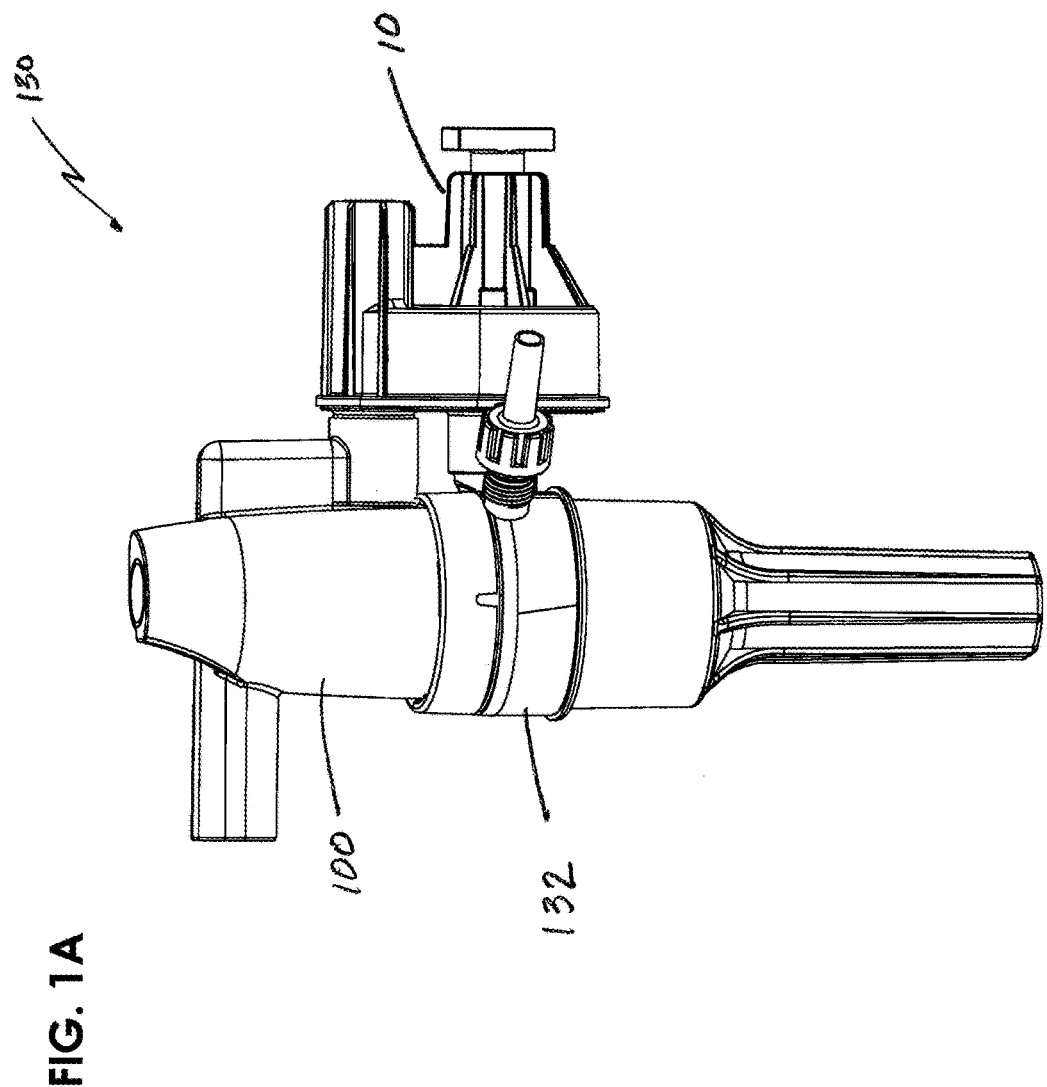
FIG. 1A is a plan view of a percussive respiratory device as shown and described in U.S. Pat. No. 6,067,984.
Figure 1B:
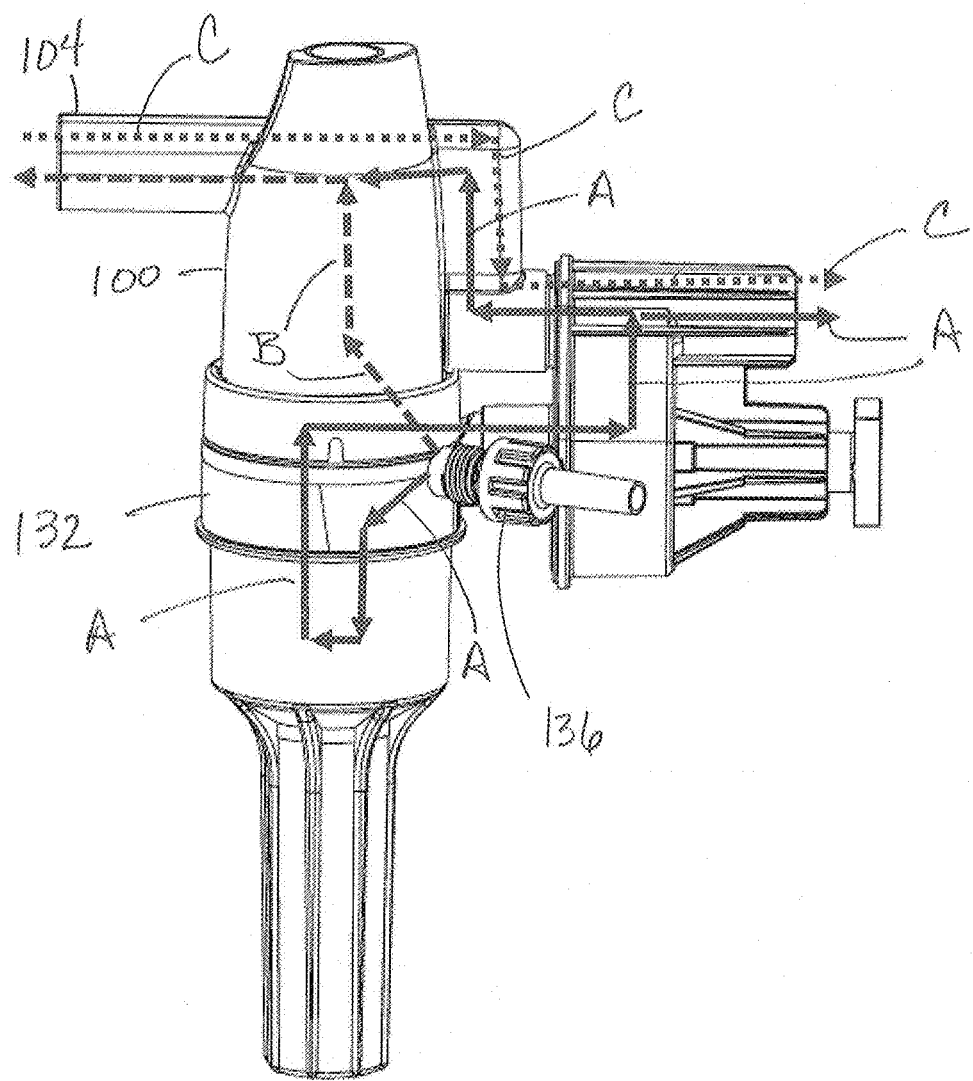
FIG. 1B is a reproduction of FIG. 1A with fluid flow paths added for purposes of explanation.
Figure 2:
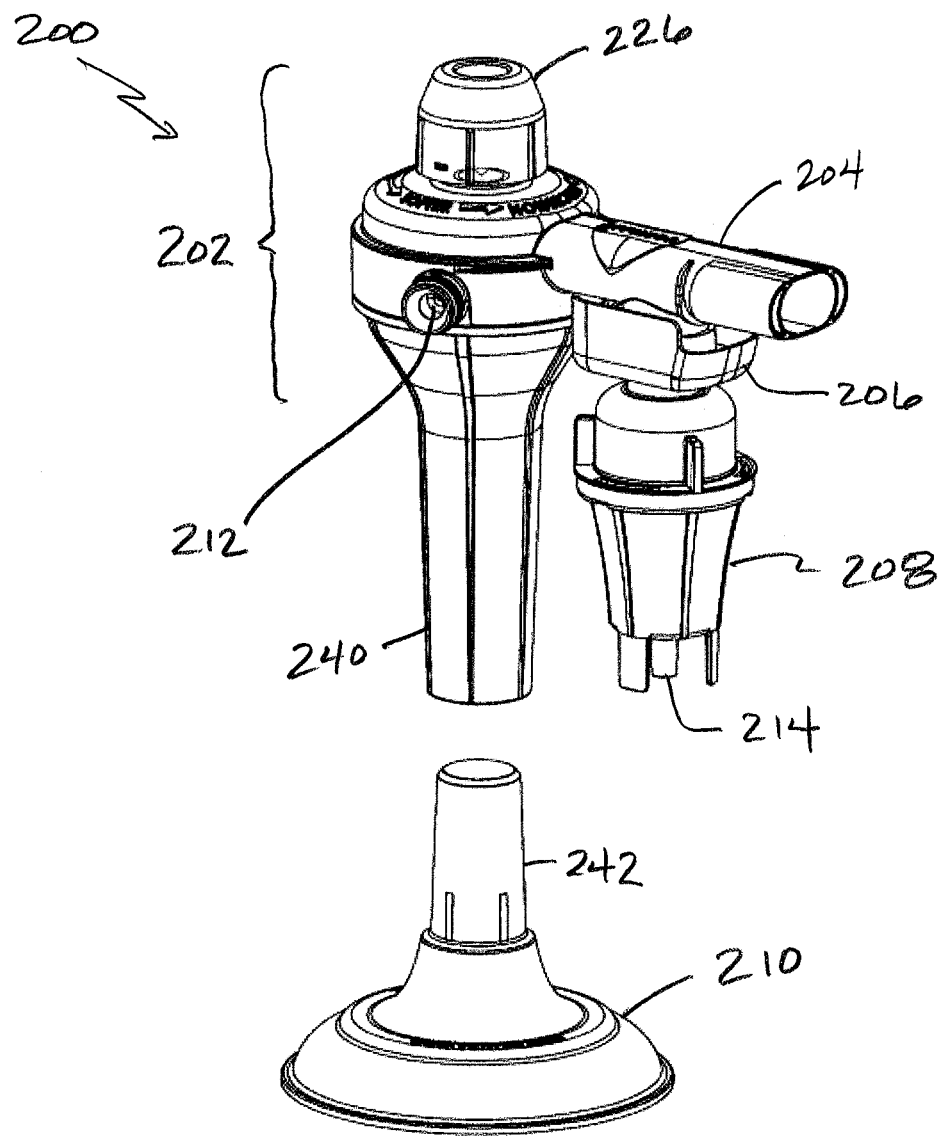
FIG. 2 is a perspective view of one embodiment of a percussive respiratory device according to aspects of the present disclosure.
Figure 3:
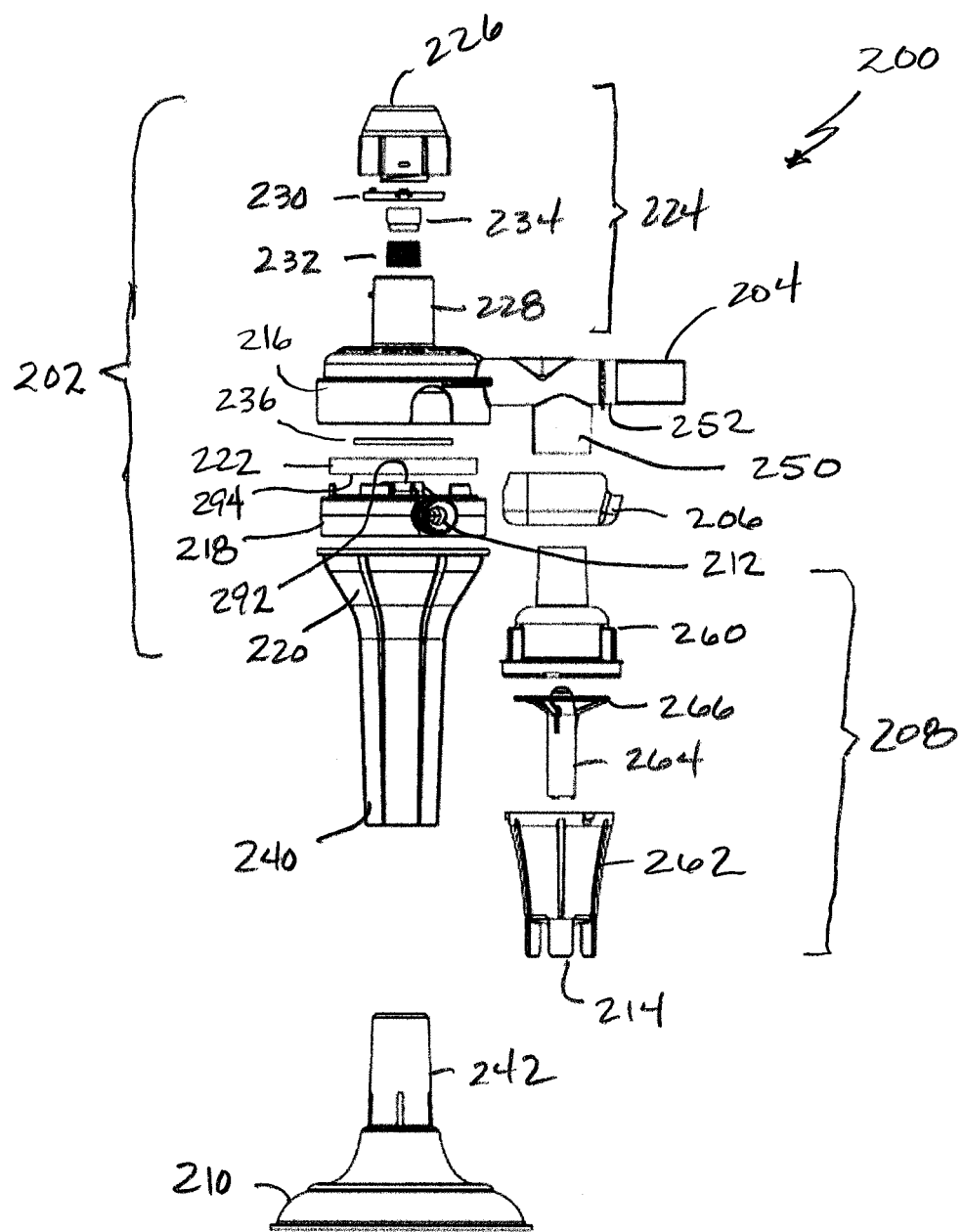
FIG. 3 is an exploded view of the device of FIG. 2.

Turning to FIGS. 2 and 3, one embodiment of a percussive respiratory device 200 according to aspects of the present disclosure is illustrated. The device 200 includes a pneumatic valve assembly 202, a patient port or mouthpiece 204, a waste or water trap 206, an optional nebulizer assembly 208 and a stand 210 for hands free use. A gas inlet port 212 supplies pressurized gas to the pneumatic valve assembly 202 and a gas inlet port 214 separately supplies pressurized gas to the nebulizer assembly 208.

The valve assembly 202 comprises a valve top 216, a valve bottom 218, a capacitor 220 and a pneumatically movable valve in the form of a diaphragm 222. The valve assembly 202 further includes a pressure modulator apparatus 224 that includes an adjustable pressure knob 226 rotatably connected to a pressure boss 228. A snap ring 230 may be used to lockably interconnect the knob 226 to the boss 228 to prevent removal of the knob. A compression spring 232 is disposed between the snap ring 230 and the diaphragm 222 and applies downward pressure on the diaphragm 222. A spring spacer 234 may be used to maintain the position of a first end of the spring 232 relative to the snap ring 230 and a washer 236 may secure the opposite end of the spring 232. A connector body 240 extends outwardly from the capacitor 220 for engaging the stand 210. As illustrated, the stand 210 comprises a cylindrical post which nests within connector body 240 to secure the percussive respiratory device in a hands-free position.

A patient mouthpiece 204 extends laterally from and is in fluid communication with the pneumatic valve assembly 202. A port 250 extends downwardly from the bottom wall 252 of the mouthpiece 204. A water or waste trap 206 is connected to the port 250 and collects fluids released or exhaled by the patient. The nebulizer assembly 208 is also in fluid communication with the mouthpiece 204 via the port 250. In one embodiment, the nebulizer assembly 208 includes male port 254 that extends through the water trap 206 and concentrically interfaces with mouthpiece port 250, allowing for exhaled body fluids to bypass the nebulizer assembly and be captured by the trap 206. The trap 206 and nebulizer assembly are removable for replacement or cleaning. The nebulizer assembly 208 includes an upper housing 260, lower housing 262 and an orifice assembly 264 with a baffle 266. As is known in the art, a liquid is placed in the nebulizer housing and compressed air or oxygen is streamed through the orifice assembly 264 to create an aerosol for inhalation by a patient. The liquid placed in the housing may optionally include a medicine for treatment of the patient or may add moisture to gas supplied to the patient.

Figure 4:
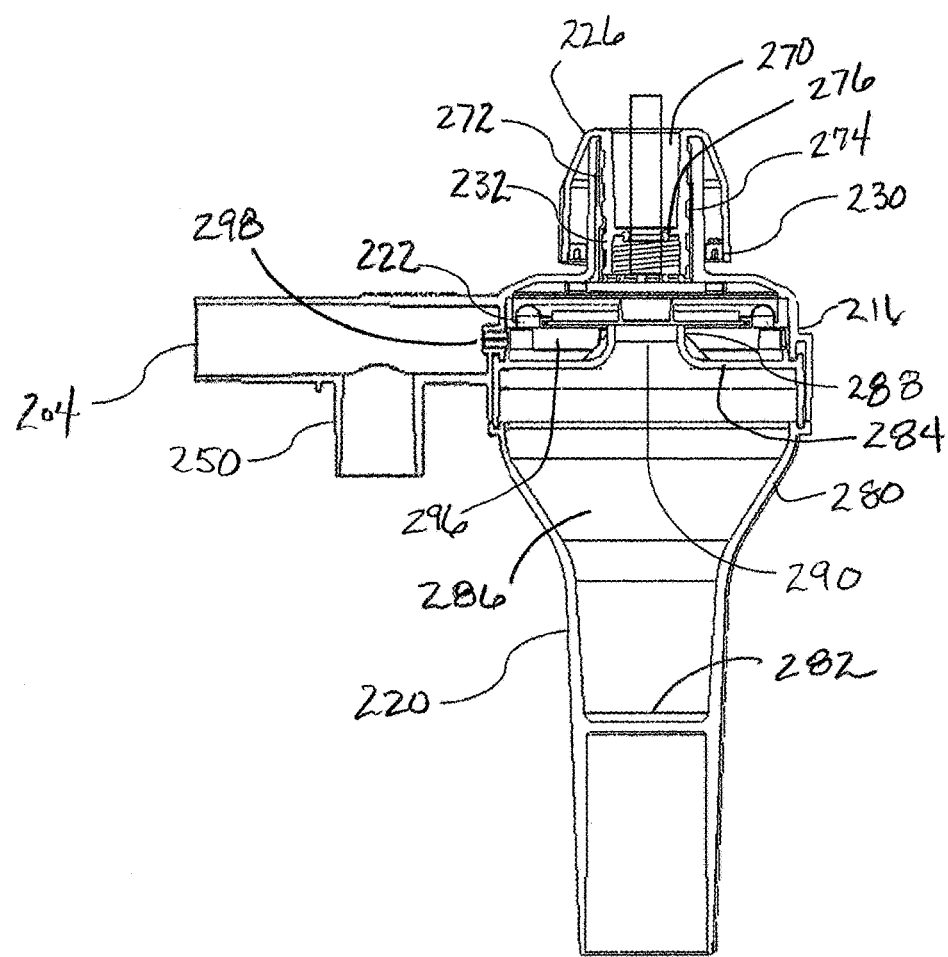
FIG. 4 is a cross-sectional view of the embodiment of FIG. 1, with the nebulizer assembly omitted.
Figure 5:
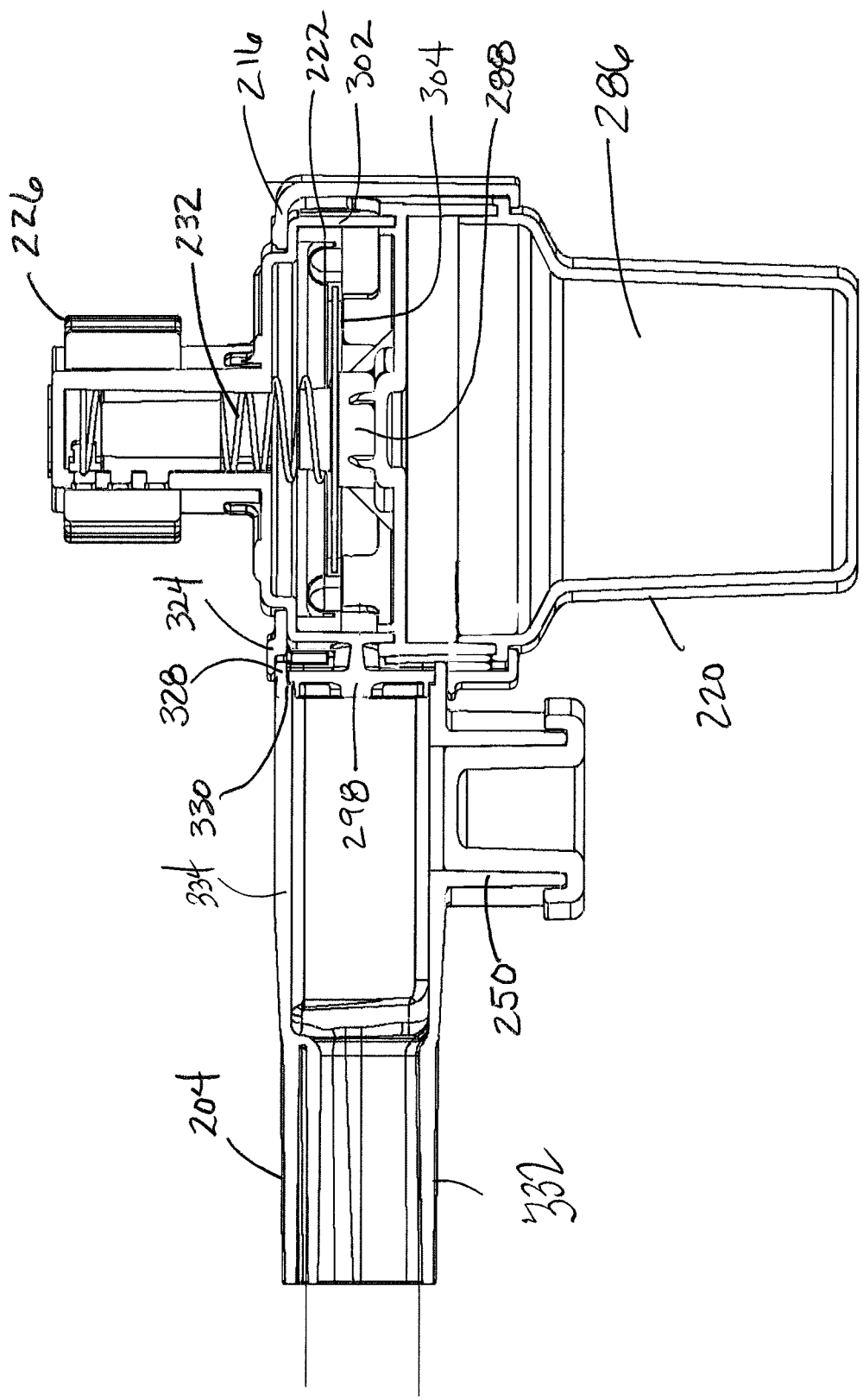
FIG. 5 is an enlarged cross-sectional view of an alternative embodiment of a pneumatic capacitive assembly for use in a percussive respiratory device.
Figure 6A:
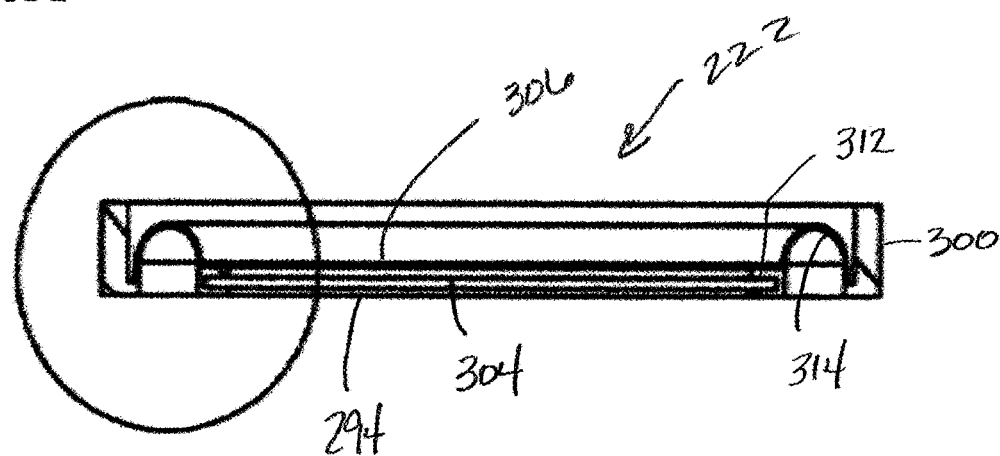
FIG. 6A is cross-sectional view of a representative diaphragm valve including a rigid center piece and a connecting web.
Figure 6B:
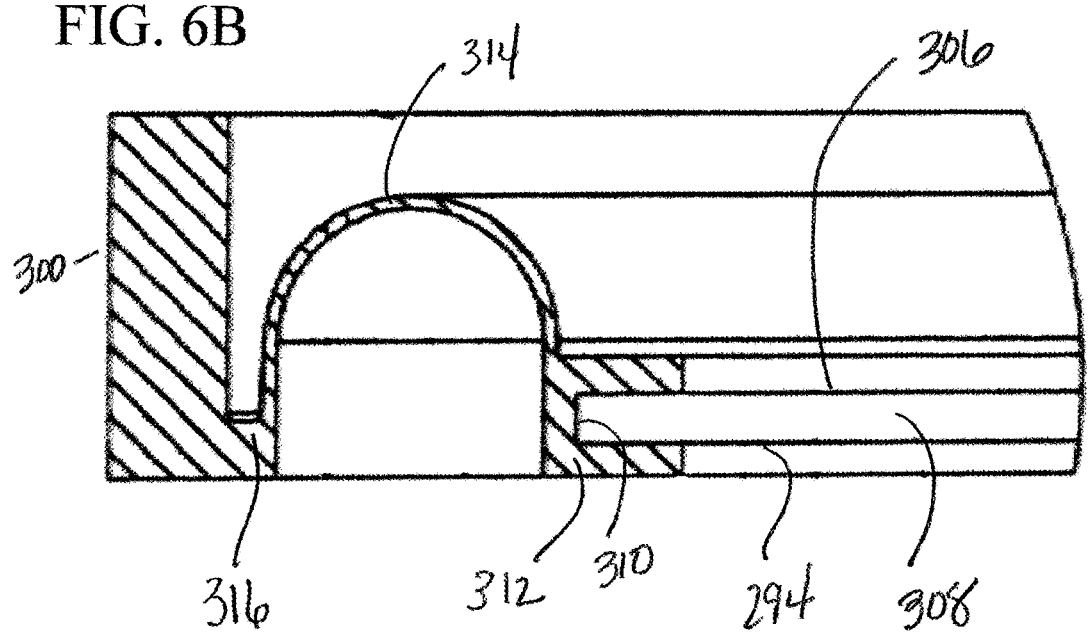
FIG. 6B is a magnified cross-sectional view of a representative diaphragm valve as depicted in FIG. 6A, including a rigid center piece and a connecting web.

Turning to FIG. 4, a cross-section of one embodiment of a percussive respiratory device according to the present disclosure is shown. The knob 226 includes a cylindrical inner wall 270 with exterior threads 272 that interface with complimentary threads 274 on the interior of boss 228. The cylindrical inner wall 270 further includes an inwardly projecting annular lip 276 that engages the top end of the spring 232. Rotating the knob 226 clockwise or counterclockwise compresses or decompresses the spring 232 to alter the pressure applied to the diaphragm 22. By adjusting the pressure applied to the upper surface of the diaphragm, the pressure opposing the opening of the diaphragm valve, the diaphragm 22 is caused to cycle at a variety of frequencies and amplitudes, thus providing a different type of ventilatory effect and therapeutic performance on the patient via the mouthpiece 204 which is in constant fluid communication with the capacitor 220 of the percussive respiratory device. Although the connection between the threads 272 and 274 is a continuous helical thread arrangement, it will be appreciated by those of skill in the art upon review of the present disclosure that other arrangements may be utilized, for example, discontinuous threads, slot and notch sliding tabs, or other such mechanisms known in the art for allowing two bodies to be affixed and adjusted in situ, and such other mechanisms are deemed within the scope of this disclosure.

In one embodiment, the position of the knob 226 may be continuously adjustable to provide continuous adjustment of the pressure applied by spring 232. Alternatively, the snap ring 230 may optionally include a suitable locking or ratchet mechanism, such as a flexible tab or spring-loaded indent, which acts upon incremental notches within the knob 226 so as to either induce a pause or requirement for additional torsion by the user to cause the knob 226 to index to the next preceding notch (either based on increasing or decreasing the compression of biasing spring 232). The notch profile may also be terminal in nature such that under normal torsion loads the knob 226 and snap ring 230 cannot be indexed further (such as at the minimum or maximum settings of the knob 226). The incremental adjustment for adding or subtracting torsion by the user allows for a percussive respiratory device 10 to be set consistently at a predefined level of therapeutic performance.

As also seen in FIG. 4, the capacitor 220 has an outer wall 280, a lower wall 282 and an upper wall 284 that define a cavity 286. The gas inlet port 212 is in fluid communication with the cavity 286. A primary port 290 is formed in the upper wall 284. In this embodiment, the port 290 is generally cylindrical in shape but may have any cross-sectional shape. The port 290 includes an upper surface 292 which interfaces with the lower surface 294 of the diaphragm 222. A secondary chamber 296 is defined by the interior of the valve top 216 and the upper wall 284 of the capacitor 220. The secondary chamber 296 is in continuous fluid communication with the interior of the patient mouthpiece 204 via port 298 in the side wall of the valve top 216.

Turning to FIGS. 5-8, the operation of one embodiment of the pneumatic valve assembly 202 according to aspects of the present disclosure will be described. The diaphragm 222 is generally cylindrical in shape with an outer wall 300 that abuts an inner surface 302 of the valve top 216 and forms a seal or fluid barrier. The diaphragm 222 further includes a central body portion 304 having an upper surface 306 and a lower surface 294. The upper surface interfaces with spring 232 and a portion of the lower surface 294 abuts the upper surface 292 of the primary port 288. The central body portion 304 comprises a disk 308 that is received in a channel or groove 310 formed in an annular ring 312. A flexible membrane 314 extends between the annular ring 312 and an inwardly projecting lip 316 formed on the inside of the outer wall 300. The flexible membrane 314 has a size and shape that allows the central body portion 304 to move linearly between an upper or open position and lower or closed position relative to outer wall 300 which is fixed and non-movable once installed. In cross-section the flexible member 314 is generally semi-circular but other shapes or sizes that allow the central portion 304 to move relative to the stationary outer wall 33 are within the scope of this disclosure.

Figure 7:
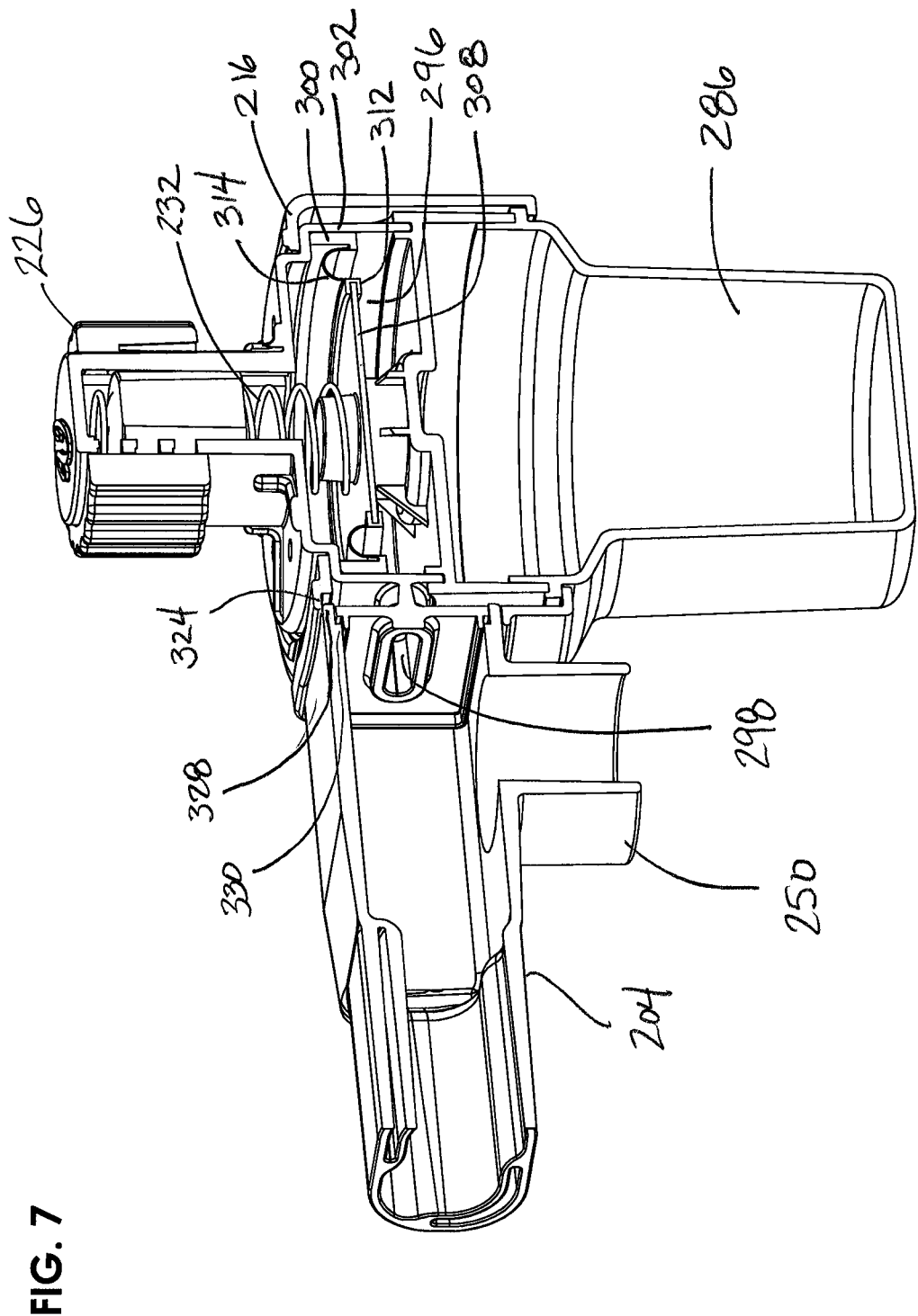
FIG. 7 is a perspective cross-sectional view of the embodiment of FIG. 5, with the diaphragm valve in a closed position.
Figure 8:
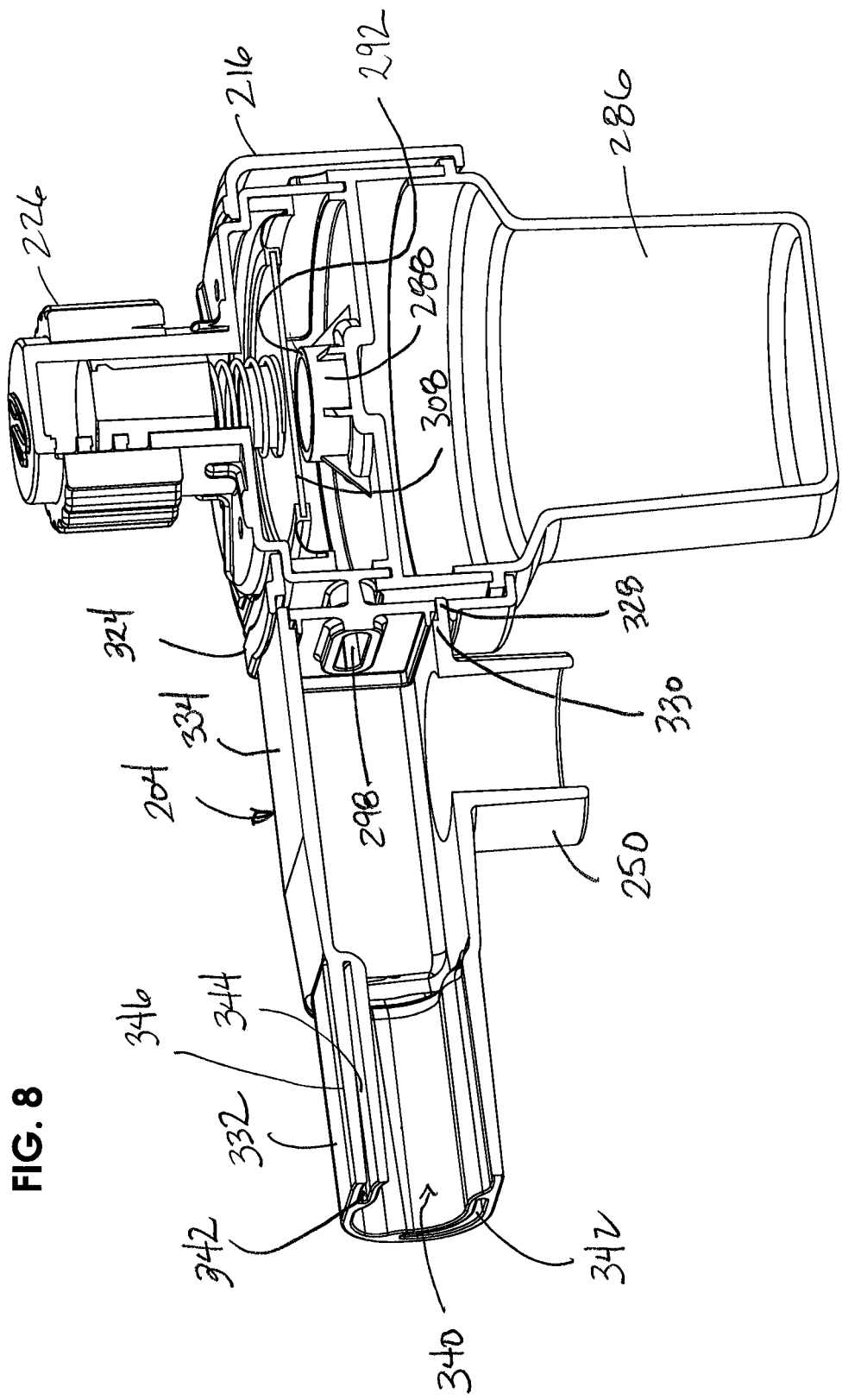
FIG. 8 is a perspective cross-sectional view of the embodiment of FIG. 5, with the diaphragm valve in an open position.

FIG. 7 illustrates the pneumatic valve assembly 202 in a closed position and FIG. 8 illustrates the valve assembly 202 in the open position. With reference to FIG. 7, the lower surface 294 of the central portion 304 of the diaphragm 222 abuts the upper surface 292 of the primary port 288 of the capacitor 220. The port 298 in the side wall of the valve top 216 is open to the mouthpiece 204 but the diaphragm 222 is blocking the port 288 due to the force applied against the upper surface 306 of the central portion 304 of the diaphragm 222 by the spring 232. Because gas is being continuously supplied to the capacitor cavity 286 through inlet port 212 the pressure within the cavity 286 builds. At some level, the pressure inside cavity 286 overcomes the force applied by the spring 232 and the central portion 304 of the diaphragm is forced up and away from the upper surface 292 of the port 288. As illustrated in FIG. 8, the flexible portion 314 of the diaphragm 222 is deformed to accommodate the movement of the central portion 304 from the closed to the open position. The central portion 304 will move from the open to the closed position upon the gas pressure within the cavity 286 decreasing below the pressure applied by the spring 232. Once the diaphragm moves to the closed position, pressure within the cavity 286 will again increase and the cycle will repeat itself. The frequency and amplitude of the movement of the diaphragm is dependent upon the pressure applied by the spring 232, which is adjustable, and the pressure of the incoming gas supply. Thus, trained personnel may adjust the frequency and amplitude of the gas supplied to a patient to achieve desired medical objectives.

In one embodiment, the diaphragm 222 exhibits a complete cycling rate of between about 1 and about 100 cycles per minute and more preferably a cycling rate of between about 10 and about 20 cycles per minute. According to aspects of the present disclosure, the diaphragm exhibits a cycling rate when provided pressurized air, oxygen or mixtures thereof at a pressure of between about 8 and about 20 cm-water and more preferably a cycling rate when provided pressurized air, oxygen or mixtures thereof at a pressure preferably between about 10 and about 18 cm-water. According to aspects of the present disclosure, the diaphragm exhibits a cycling rate when provided pressurized air, oxygen or mixtures thereof at a flow of between about 8 and about 30 liters per minute and more preferably a flow of preferably between about 10 and about 25 liters per minute.

Figure 9:
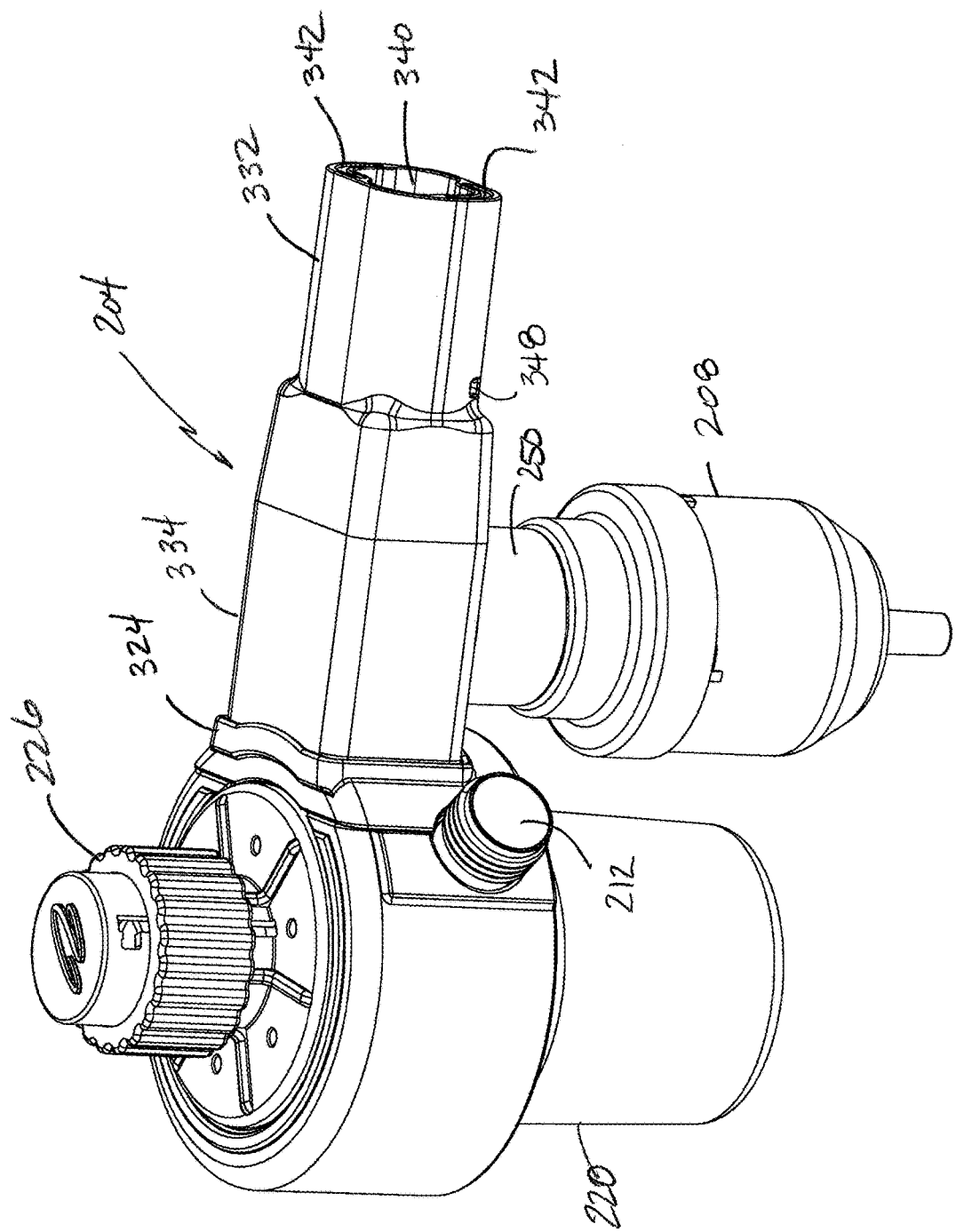
FIG. 9 is a perspective view of the embodiment of FIG. 5, with a nebulizer assembly attached to the underneath or lower side of the patient mouthpiece.
Figure 10:
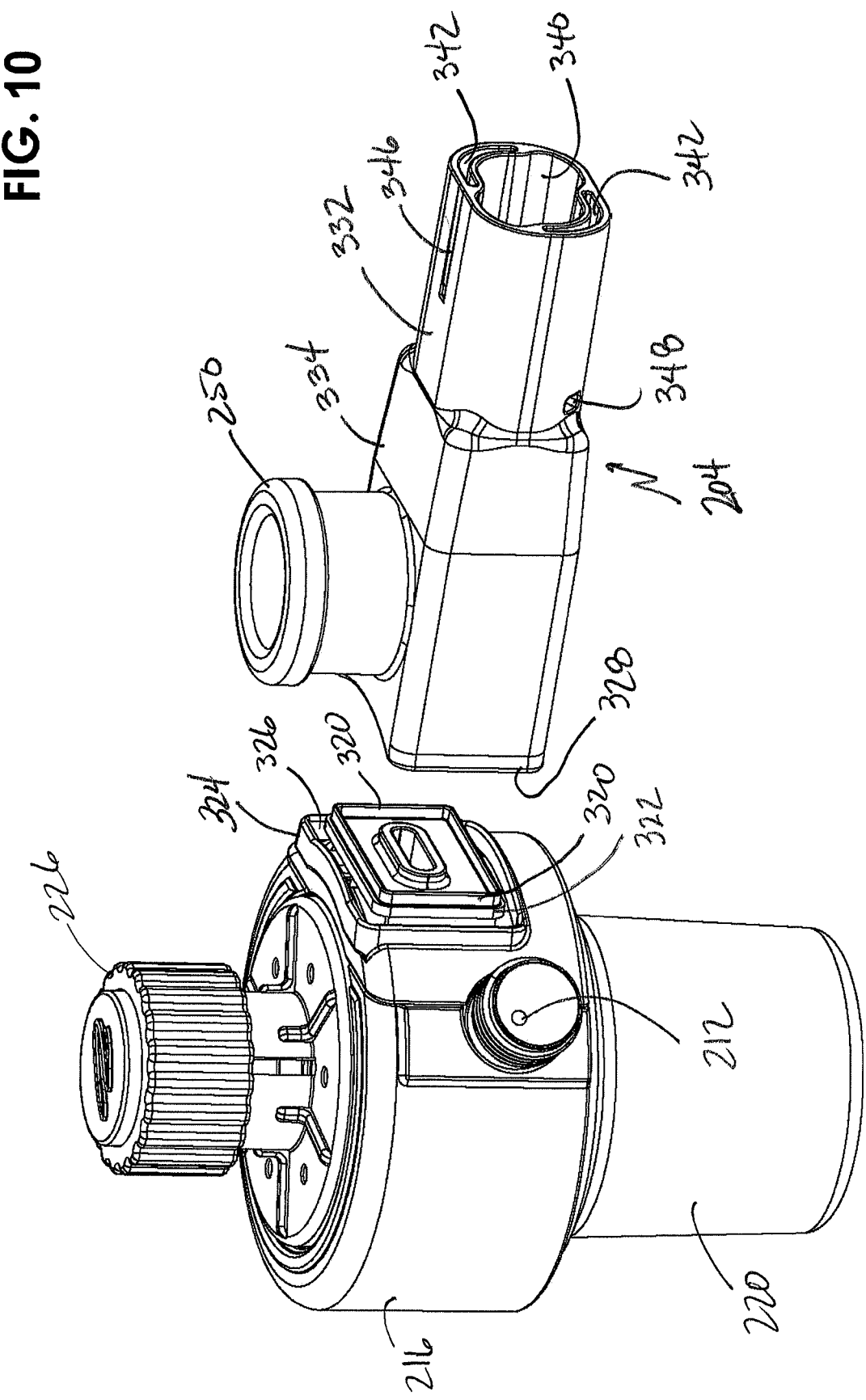
FIG. 10 is a perspective view of the embodiment of FIG. 5, with the patient mouthpiece rotated 180 degrees and separated from the pneumatic valve assembly compared to FIG. 9, such that a nebulizer assembly may be connected to the top or upper side of the mouthpiece.

FIGS. 9-10 illustrate the reversible nature of the mouthpiece 204 according to aspects of the present disclosure. The mouthpiece is generally symmetrically designed such that the port 250 may be oriented on the bottom (FIG. 9) or the top (FIG. 10). In turn, this provides flexibility when utilizing nebulizers. Some nebulizers are designed for a bottom position, for example, VixOne nebulizer sold by Westmed, Inc., Tucson, Ariz. And other nebulizers, for example, Aerogen Solo manufactured by Aerogen, Galway, Ireland are designed for a top or upper position. A friction fit connection scheme allows the mouthpiece 204 to be secured to the outer wall of the valve top 216 in either orientation. Stepped shoulders 320 and 322 protrude or extend from the side wall of the valve top 216. These shoulders are positioned within a protruding perimeter wall 324 and a channel 326 is formed between the perimeter wall 324 and the shoulders 320 and 322. In contrast, the open end of the mouthpiece 204 that mates with the valve top 216 comprises a perimeter edge or lip 328 and an inner shoulder 330 as best seen in FIGS. 7 and 8.

Figure 11A:
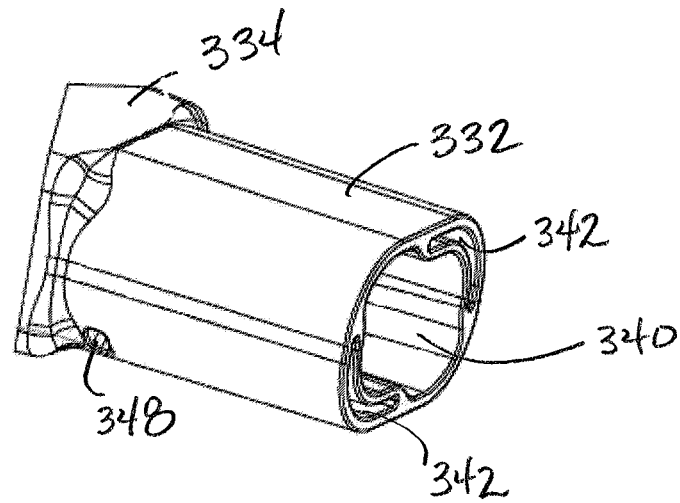
FIGS. 11A-C are alternative embodiments of a patient mouthpiece with a dual lumen.
Figure 11B:
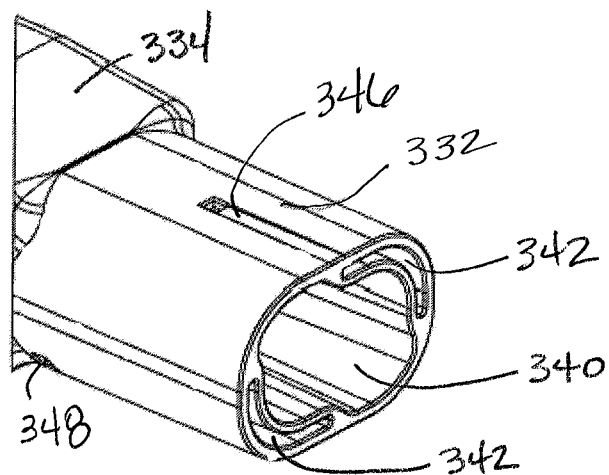
Figure 11C:
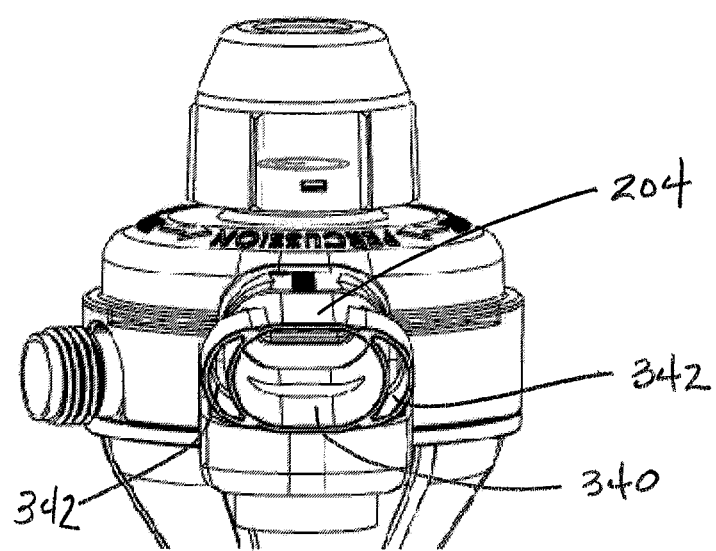

Another feature of a percussive respiratory device according to aspects of the present disclosure is the multiple pathway or multiple lumen design of the mouthpiece 204. As seen in FIG. 10, for example, the mouthpiece 204 has a proximal body portion 332 that interfaces with a patient and a distal body portion 334 that interfaces with the valve assembly 202. The proximal body portion 332 is reduced in overall size relative to the distal body portion 334 to ergonomically accommodate and interface with the mouth of a patient. As seen in FIGS. 11A-C, the proximal end 332 of the mouthpiece 204 includes multiple fluid flow pathways or lumens. A first lumen 340, centrally located, delivers input gas to the patient. One or more second lumens 342, located outside or peripheral to the central lumen 340, transport exhalation from a patient and vent it to atmosphere. As illustrated in FIGS. 7 and 8, the outer lumens 342 form a channel 344 along the interior of the proximal body portion 332. In the embodiment of FIG. 11A, an exit hole or port 348 in the proximal body portion 332 is in fluid communication with each outer lumen 342 and provides an exit path to atmosphere for exhalation. As illustrated in FIG. 11B, a slot 348 optionally may be formed in the proximal body portion 332 in fluid communication with the channel 344 to allow exhalation to exit the mouthpiece. In FIGS. 11A and 11B, the outer lumens 340 are oriented in opposite corners of the proximal body portion 332. In the embodiment of FIG. 11C, the lumens are oriented on opposite sides of the proximal body portion 332. It should be appreciated that the outer lumens may comprise other shapes than illustrated, that there may be one, two, three or more outer lumens and the outer lumens need not be positioned at the outer perimeter of the proximal body portion 332. For example, outer lumen(s) 342 may be oriented on one side of the proximal body portion 332 and the inhalation lumen 340 oriented on the opposite side. The single input lumen 340 may also comprise multiple lumens. In addition, the walls of the lumens may be configured by shape, orientation and/or surface texture to create with turbulence or laminar flow of the input gas and exhalation to optimize treatment for any given patient.

In operation, a patient receives treatment of a fluidic source through the first lumen, with the first lumen being of a size and geometry so as to not create an excessively high flow or pressure of the fluid which might cause undue physiological harm. Upon exhalation or exhaust of the fluid from the patient, the fluid is directed through the second lumen and away from the patient via an exteriorly associated exhalation port 346 or slot 344. The exhalation port or slot may be in direct communication with the ambient environment of the patient, or may route through a secondary process, such as a gas scavenging system or a filter, so as to reclaim or extraction one or more fractions of the exhaust flow. It is within the prevue of the present disclosure that the first and second lumens may be in a circumferential, "side by side", or alternate relationship, and that either or both lumens may have the same or different geometries, and may be further divided into one or more secondary routings or sublumens that provide the same or alternate flows of the same or different fluidic sources.

Figure 12B:
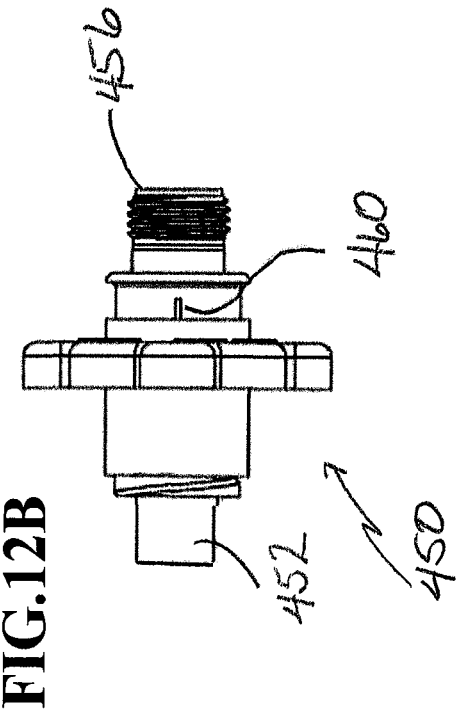
FIG. 12B is an elevation view of the embodiment of FIG. 12A.
Figure 12C:
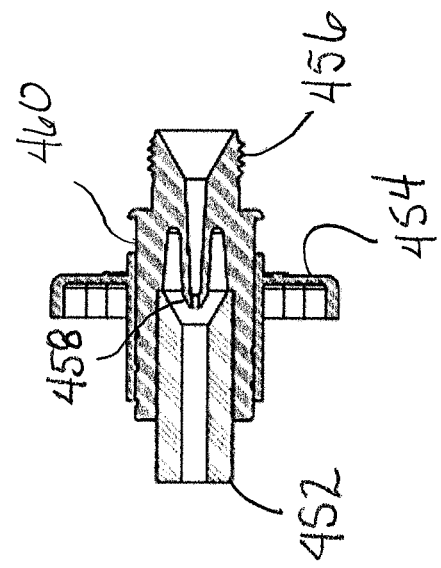
FIG. 12C is a cross-sectional view of the embodiment of FIG. 12B.
Figure 12A:
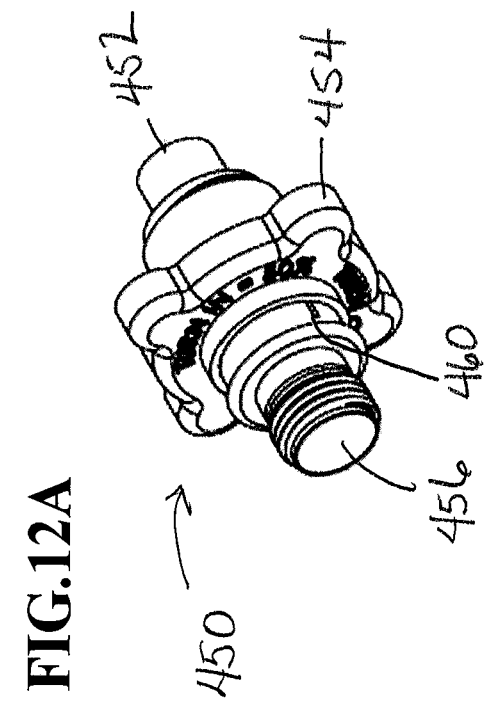
FIG. 12 A is a perspective view of one embodiment of an entrainment device.

A further element of the present invention comprises a variable entrainment valve assembly 450 illustrated in FIGS. 12A-C. The entrainment valve assembly 450 includes an entrainment gas inlet port 456 where by a pressurized fluid source in connected, for example, an air compressor or pressurized oxygen tank (not shown). Pressurized fluid is conducted through the inlet port 456 and through an entrainment jet 458. The entrainment jet 458 imparts a laminar flow to the pressurized fluid whereby it is conducted into a entrainment outlet port 452. According to aspects of the present disclosure, in at least one embodiment, outlet port 452 is in fluid communication with an inlet port of a percussive respiratory device, for example port 212 shown in FIG. 2. As the laminar flow is conducted from the inlet port 456 to the outlet port 452, a negative pressure is created proximal to the entrainment jet 458. Fluid is drawn in by the negative pressure through one or more secondary inlet ports 460. The degree of flow through the one or more secondary inlet ports 460 is defined by an entrainment mixing adjustment 454 which engages upon an indexing element 462 exterior to entrainment gas outlet port 452 to allow for finite adjustment. The volume of fluid conducted through the entrainment gas inlet port 456 plus the volume of fluid drawn in by the secondary inlet port 460 are intermixed and ejected as an essential homogenous fluid via the entrainment jet outlet port 452. Gas entrainment valve assembly 450 is designed such that indexing the assembly by rotation of the entrainment mixing adjustment 454 either increases or decreases the volume of atmosphere which can be drawing into the assembly. In one embodiment, the indexing element the indexing element ranges from fully closed to fully open in about 360 degrees or less rotation about said entrainment jet. Alternatively, the indexing element 462 ranges from fully closed to fully open in about 270 degrees or less rotation, or in about 180 degrees or less of rotation, or in about 90 degrees or less of rotation.

Representative relative fluidic mixing ratios include those shown in Table 1.

TABLE 1

| Rotation Angle | Travel (in) |
|---|---|
| 25 | 0.014 |
| 45 | 0.025 |
| 90 | 0.05 |
| 135 | 0.075 |
| 225 | 0.125 |
| 270 | 0.15 |

According to aspects of the present disclosure, in one embodiment, the entrainment valve 450 exhibits a ratio of pressurized fluid to volume of fluid drawn in by the secondary inlet port of between about 10:90 to about 90:10 and more preferably a ratio of pressurized fluid to volume of fluid drawn preferably in by the secondary inlet port of between about 30:70 to about 70:30. Accordingly, with the entrainment valve operatively connected to a percussive respiratory device, the volume or rate at which compressed gas is supplied to the percussive respiratory device may be decreased without loss of functionality. For example, a percussive respiratory device in combination with a nebulizer typically requires a flow of about 25 to 30 liters per minute (LPM) to function properly. When an entrainment valve of the type described herein, e.g., valve 450, is connected to the inlet port 212 of a capacitor 220, flow requirements can decrease to approximately 10-12 LPM with room air added to the input gas through ports 458. This allows potentially for less consumption of supplied input gas and also increases the use of the percussive respiratory device outside of hospitals, nursing homes and other medical facilities allowing the device to be used in private settings and residences where high flow rate input gas sources are not readily available. Instead, the percussive respiratory device may be used with a smaller compressor capable of satisfying the lower flow rate requirements. Lower flow rate compressors are more readily available, including from most home healthcare companies, are less expensive that high flow rate compressors and are typically covered by private insurance.

It is within the purview of the present invention that the individual components of the percussive respiratory device may be constructed from thermoplastic and/or thermoset polymers, nonferrous metals, ferrous metals, glass, and the combinations thereof. The present invention is not constrained to the mode or method of individual component manufacture, such as by molding or machining, or by the means such components are combined into the apparatus depicted, such as by adhesives (gluing), thermal welding (i.e. ultrasonic), or mechanical retention (screws, interlocking tabs, clasps).

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

The foregoing Detailed Discussion has been presented for purposes of illustration and description. The foregoing is not intended to limit the invention to the form or forms disclosed herein. For example, various features are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

What is claimed is:

1. A percussive respiratory apparatus, comprising:
    a pneumatic valve assembly having a housing, a diaphragm positioned in the housing that moves between a first position and a second position, a first fluidic communication port, wherein the diaphragm abuts and closes the fluidic communication port when in the first position and is spaced from the first fluidic communication port in the second position, and a second fluidic communication port spaced from the first fluidic communication port;
    a biasing member positioned on a first side of the diaphragm and applying a force on the diaphragm to move the diaphragm from the second position to the first position;
    an adjustable knob associated with the biasing member to vary the force applied by the biasing member on the diaphragm;
    a gas receiving chamber in fluidic communication with the first fluidic communication port;
    a patient interface in fluid communication with the second fluidic communication port, wherein the patient interface includes a divided lumen having at least a first pathway adapted to provide an inhalation fluid and at least a second pathway adapted to channel exhalation fluid away from a patient;
    wherein when the diaphragm moves from the first position gas within the gas receiving chamber moves through the first and second fluidic communication ports to the patient interface through at least the first pathway, when the diaphragm is in the first position, no gas exits the receiving chamber, and at least the second pathway is configured to receive gas exhaled from a patient.

2. The apparatus of claim 1, wherein said receiving chamber is a pneumatic capacitor and has a dynamic variable response.

3. The apparatus of claim 1, wherein the adjustable knob allows for finite control of the movement of the diaphragm to create an oscillating movement in terms of frequency of cycling, amplitude of each cycle, and the combinations thereof.

4. The apparatus of claim 1, wherein the diaphragm exhibits a complete cycling rate of between about 1 and about 100 cycles per minute when provided pressurized gas at a flow rate of between about 8 and about 30 liters per minute.

5. The apparatus of claim 1, wherein the diaphragm exhibits a cycling rate when the gas receiving chamber is provided pressurized gas at a pressure of between about 8 and about 20 cm-water.

6. The apparatus of claim 1, wherein the diaphragm exhibits a cycling rate when provided pressurized gas at a flow of between about 8 and about 30 liters per minute.

7. The apparatus of claim 1, further comprising an entrainment valve assembly in fluid communication with the gas receiving chamber, and having a third fluidic communication port drawing fluid into the entrainment valve assembly from a source external to the entrainment valve assembly.

8. The apparatus of claim 7, wherein said entrainment valve creates a negative pressure which induces additional fluid to be draw into the apparatus.

9. The apparatus of claim 8, wherein a ratio of pressurized fluid to volume of fluid drawn in by the third fluidic communication port is between about 10:90 to about 90:10.

10. The apparatus of claim 1, further comprising a nebulizer assembly in fluid communication with the patient interface.

11. The apparatus of claim 10, wherein the patient interface is repositionable to allow the nebulizer assembly to be repositioned relative to the apparatus itself.

12. The apparatus of claim 11, wherein the patient interface includes a fourth fluidic communication port for operative association with the nebulizer assembly, and wherein repositioning the patient interface repositions the fourth fluidic communication port.

13. The apparatus of claim 1, wherein the at least one second pathway comprises at least one ventilation port.

14. The apparatus of claim 1, wherein the at least first and at least second pathways are in symmetrical orientation as viewed in cross-section of the divided lumen.

15. The apparatus of claim 7, wherein the entrainment valve assembly, comprises:

(a) a pressurized fluid source;

(b) an entrainment gas inlet port;

(c) an entrainment jet;

(d) the third fluidic communication port;

(e) a secondary fluid source; and (f) an entrainment outlet port;

(g) wherein the pressurized fluid source flows through the entrainment gas inlet port and into the entrainment jet, wherein the entrainment jet imparts a laminar flow on the pressurized fluid, wherein the laminar flow of pressurized fluid leaves the entrainment valve assembly through the entrainment outlet port, wherein the laminar flow creates a negative pressure proximal to the entrainment jet and before the entrainment outlet port, and wherein the negative pressure causes fluid to be drawn in through the secondary inlet port and to become entrained into the laminar flow of the pressurized fluid source.

16. The apparatus of claim 15, wherein the entrainment valve assembly further comprises an indexing element, wherein the indexing element allows for the ratio of entrainment of secondary fluid source to said pressurized fluid source to be finitely controlled.

17. The apparatus of claim 16, wherein the indexing element circumscribes the entrainment jet.

18. The apparatus of claim 16, wherein the indexing element ranges from fully closed to fully open in about 270 degrees or less rotation about the entrainment jet.

19. The apparatus of claim 15, wherein the pressurized fluid and said secondary fluid source leave the entrainment valve assembly as an essentially homogenous fluid mixture.

20. The apparatus of claim 15, wherein the secondary fluid source is ambient air.

* * * * *